United States Patent [19]

Lopukhin et al.

[11] 4,377,511
[45] Mar. 22, 1983

[54] PREPARATION FOR CONTROL OF T-SYSTEM OF IMMUNITY AND METHOD FOR PRODUCING SAME

[76] Inventors: Jury M. Lopukhin, Kutuzovsky prospekt, 45, kv. 31; Rem V. Petrov, Zhivopisnaya ulitsa, 50, kv. 43; Vitaly Y. Arion, Teply stan, 9 mikroraion, korpus 4, kv. 120; Jury N. Breusov, Belovezhskaya ulitsa, 49, kv. 30; Tatyana V. Gladysheva, ulitsa Volgina, 39, kv. 25; Irina V. Sanina, ulitsa Koptevskaya, 18v, kv. 126; Vasily V. Lebedev, Teply stan, 9 mikroraion, korpus 4, kv. 118, all of Moscos; Serafima S. Kirzon, Moskovskaya oblast, ulitsa Pobedy, 18, kv. 55, Balashikha; Evgeny F. Ivanushkin, ulitsa Godovikova, 16, kv. 18, Moscow, all of U.S.S.R.

[21] Appl. No.: 203,347

[22] Filed: Nov. 3, 1980

[51] Int. Cl.$^3$ .................. C07G 7/00; A61K 37/00
[52] U.S. Cl. ......................... 260/112 R; 424/177
[58] Field of Search .................... 424/177; 260/112 R

[56] References Cited

U.S. PATENT DOCUMENTS

| | | | |
|---|---|---|---|
| 4,002,740 | 1/1977 | Goldstein et al. | 424/177 |
| 4,010,148 | 3/1977 | Goldstein | 260/112 R |
| 4,079,127 | 3/1978 | Goldstein et al. | 424/177 |
| 4,120,951 | 10/1978 | Goldstein | 424/177 |
| 4,128,637 | 12/1978 | Naylor et al. | 424/177 |
| 4,239,498 | 12/1980 | Rule | 260/112 R |

OTHER PUBLICATIONS

J. of Immunology 117, No. 1, (1976), 313–318.
Khaw, et al., Br. J. Cancer, (1973), 28, 288–292.
Miller, et al., Annals New York Academy of Science, 54–60.
Miller, et al., J. of Immunology 111, (1973), 1005–1009.
Goldstein, et al., Biochemistry, (1966), 1010–1017, vol. 56.
Nathenson, et al., Microbiology 56, 1966, 476–483.
Assaker, et al., Immunology 5158.
Annals New York Academy of Sciences, 234–240.
Goldstein, Triangle, vol. 11, No. 1, (1972), 7–14.
Goldstein, The Lancet, (1968), 119–122.
Goldstein, Nature 247, (1974), 11–14.
Chem. Abstr. 75, 1971, 2264m.
Chem Abstr. 74, 1971, 74202s.
Chem. Abstr. 74, 1971, 107464i.
Chem. Abstr. 67, 1967, 89620f.
Chem. Abstr. 67, 1967, 9611r.
Chem. Abstr. 73, 1970, 75216r.
Chem. Abstr. 73, 1970, 128537e.
Chem. Abstr. 82, (1975), 52001p.
Chem. Abstr. 82, 1975, 168226v.
Chem. Abstr. 83, 1975, 76888e.
Chem. Abstr. 81, 1974, 48075c.
Chem. Abstr. 92, 1980, 213364h.
Chem. Abstr. 92, 1980, 116412q.
Chem. Abstr. 81, 1974, 75518f.
Chem. Abstr. 87, 1977, 83044n.
Chem. Abstr. 80, 1974, 131090d.
Chem. Abstr. 79, 1973, 61811t.
Chem. Abstr. 87, 1977, 199009j.
Chem. Abstr. 93, 1980, 62101n.

*Primary Examiner*—Delbert R. Phillips
*Attorney, Agent, or Firm*—Steinberg & Raskin

[57] ABSTRACT

The present invention relates to immunopharmacology and, more specifically, to a preparation controlling the T-system of immunity and to a method for producing the same.

The preparation controlling the T-system of immunity is characterized by its content as the active principle, peptides with a molecular mass of from 1,500 to 6,000 Dalton having absorption maximum in UV-light at 280 and 275 nm and electrophoretic mobility in a polyacrylamide gel relative to bromophenol blue: 0.062–0.102; 0.156–0.236; 0.354–0.374; 0.382–0.422; 0.432–0.472; 0.485–0.545; 0.850–0.930.

The method for producing the preparation according to the present invention comprises homogenization of a tissue of thymus gland in a solution of sodium chloride; the homogenizate is kept for 12–16 hours at a temperature of from 2° to 6° C., the residue is removed, thermolabile proteins are removed from the solution, peptides
} and proteins are precipitated and then dissolved and peptides are salted-out from the solution successively in three stages, the residue of peptides is removed, ultrafiltered through a membrane with a rated retention limit relative to globular proteins of from 12,000 to 30,000, the ultrafiltrate is gel-chromatographed to isolate peptides with a molecular mass of from 1,500 to 6,000 Dalton, desalted and lyophilized.

This preparation is used for the treatment of primary and secondary immunodeficient states, diseases caused by malignant neoplasms, psoriasis and other pathological states.

9 Claims, 4 Drawing Figures

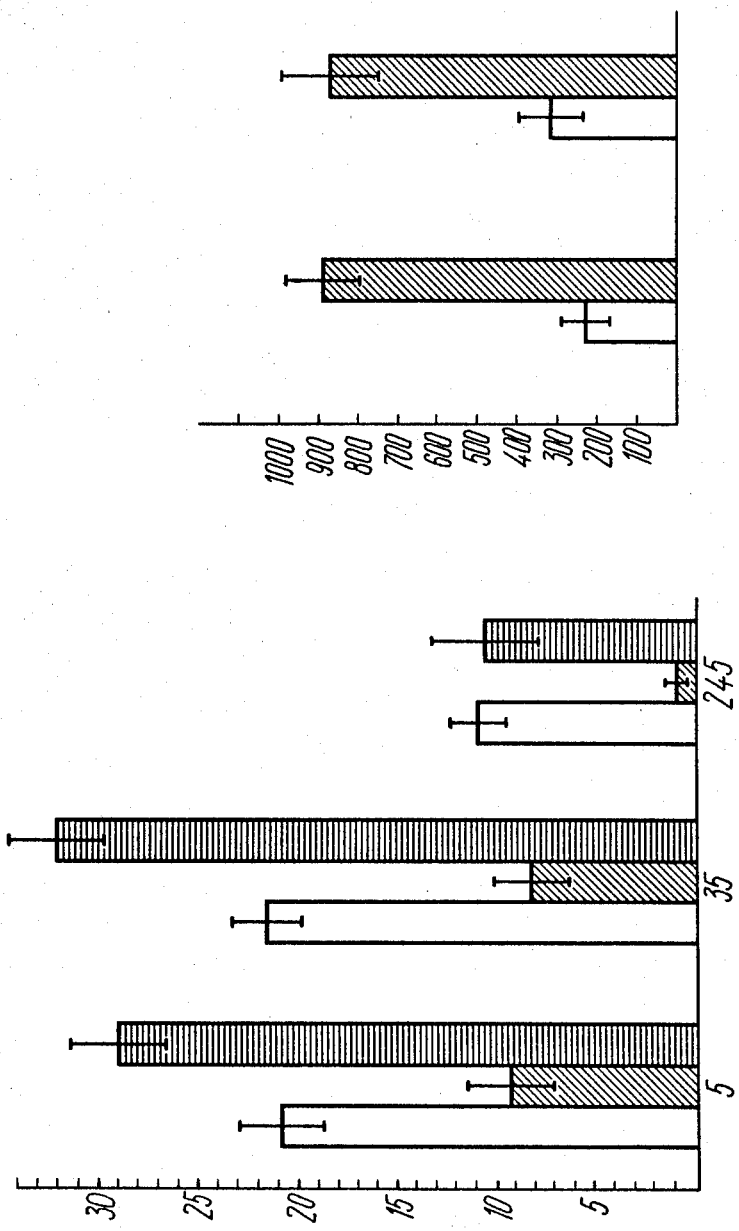

PREPARATION FOR CONTROL OF T-SYSTEM OF IMMUNITY AND METHOD FOR PRODUCING SAME

FIELD OF THE INVENTION

The present invention relates to medicine and, more specifically to immunopharmacology, in particular to a preparation for controlling the T-system of immunity and to a method for producing same.

The preparation is useful in the treatment of primary and secondary immunodeficiency states. The preparation contributes to restoration of immunohomeostasis of the organism and exerts a regulating effect on the immune and hematoplastic systems.

This invention relates, first of all, to T-lymphocytes and restoration of the balance of different sub-populations of the T-system of immunity, thus providing an implicit influence on the B-system of immunity. Consequently, the preparation according to the present invention is useful in clinics for the restoration of disturbances of the T-system of immunity functions. This applies, first of all, to such well known disturbances of the immune system in various tumors, congenital immunodeficient pathology (for example with manifestation of Louis-Bar syndrome), acute viral infection (for example, Herpes Zoster) and some other diseases associated with the immune status disturbance such as psoriasis, systemic lupus erythematosis.

BACKGROUND OF THE INVENTION

First attempts to restore the immunity system in primary and secondary immunodeficiency states have been made by way of transplantation of embryonal or neonatal thymus, and thymus in combination with sternum (cf. Yu. M. Lopukhin, Yu. I. Morozov, R. V. Petrov "Actual Problems of Transplantation of Organs", Moscow, 1974, pp. 286–302). In patients suffering from ataxia-telangiectasia (Louis-Bar syndrome), a genetic disease associated with disturbance of the function of T-cells in absence of immunoglobulins A and E (IgA, AgE), the transplantation of thymus causes a partial restoration of immunocompetence and a positive clinical dynamics. However, along with the tissue of the implanted thymus, numerous biochemical compounds are introduced into the body and a portion thereof can be toxic for the recipient. Insufficient vascularization, origination of immunological conflict are responsible for a rapid deterioration of the transplant. In transplantation of thymus it is impossible to ensure dosage of the active principle into the patient's organism. For this reason, the therapeutic effect in transplantation of thymus is but a short-termed and not always clearly pronounced. All these factors necessitate the production of preparations from thymus, or from other organs which should possess a considerably higher biological activity, a wide range of the therapeutic effect relative to primary and secondary immunodeficiency states caused by various external factors, malignant neoplasms having no immunogenic properties and causing no complications upon administration.

In the investigation of the preparation produced from thymus it has been found that its biological activity is due to the protein with the molecular mass of 12,600 Dalton. The method for producing the preparation involves homogenization of the tissue of thymus gland in NaCl, the removal of a residue from the homogenate, separation of thermolabile proteins from the solution, precipitation of proteins and peptides from the solution, dissolution of the precipitated proteins and peptides, salting-out of the peptides, dissolution of the residue of peptides, desalting of the separated peptides and lyophilization thereof (cf. Goldstein A. L., Guha A., et al., Proc. Natl. Acad. Sci. USA, 69, p.1800, 1972).

Further investigations have shown that the protein comprises an aggregation consisting of a number of polypeptides with a molecular mass of below 1,000 Dalton (cf. Hopper J. A., McDaniel M. C., et al., Ann. N.Y. Acad. Sci., 249, p.125, 1975).

Disk-electrophoresis in a polyacrylamide gel and isoelectric focusing in ampholines have made it possible to identify individual polypeptides. The biologically active fraction of thymosin (V fraction) has more than 20 components with a molecular mass of from 1,000 to 15,000 Dalton. It should be noted that certain polypeptide fractions of the preparation of thymus or combinations thereof have different biological activity in immunological tests in vivo and in vitro. Thus, the highest activity in the test of inhibition of migration of lymphocytes is manifested by $\alpha$-thymosin with the molecular mass of 3,108 and pI of 4.2 (cf. Low, T. L. K., Goldstein A. L. In: The Year in Hematology; R. Silber, J. Lobuc, A. S. Gordon, eds) pp. 281–319, Plenum Publishing, New York, 1978). Other peptides produced from thymus, e.g. $\beta_3$ and $\beta_4$ induce the synthesis of the termonal desoxynucleotidyltransferase in precursors of T-cells. A number of polypeptides of thymus such as $\beta_1$ are fully identical with biologically active peptides of other organs and, in particular, ubiquitin (cf. U.S. Pat. No. 4,002,602, 1977). Ubiquitin is capable of causing expression of T and B cell markers in vitro by activation of the adenylatecyclase cycle and influencing on $\beta$-adrenergic receptors.

Also known is a thymic humoral factor capable of inducing immunocompetent cells in vitro by sensitivity of rosette-forming cells (E-RFC) in respect of azotioprin. The molecular mass of the humoral factor is about 56,700 Dalton; in fractions with a lower molecular mass there have been found only traces of biological activity (cf. White A. In: Biochemical Action of Hormones (G. Lidruk, ed.), Vol. 7, Academic Press, N.Y., 1979).

Therefore, thymus peptides, polypeptides and proteins have a too wide heterogeneity both in molecule size and biological properties thereof. It is obvious that a medical preparation based on peptides and possessing an effective action should contain molecules with a specific molecular mass and a sufficiently high biological activity. In this case a unique composition of peptides defines the range and efficiency of their therapeutic effect. The biological activity of peptides can be enhanced in principle by way of an additional purification, or by their chemical or enzymatic modification. The attempts of clinical application of the preparations containing polypeptides for stimulation of the T-system of immunity have been undertaken on patients suffering from primary and secondary immunodeficient states. In the case of the primary immunodeficient state (thymus hypoplasia) after the administration of a preparation containing thymus polypeptides the patient's condition is improved. However, directly after completion of the course of immunotherapy the patient's condition is sharply declined (cf. Goldstein A. L. et al., Transplant. Proc., V.7, pp. 681–686, 1975).

In secondary immunodeficient states caused by malignant tumors, the administration of the preparation containing polypeptides (V-fraction of thymus) has given a positive effect only in 5 patients out of 32 leukemia-suffering patients. In a patient with chorion-epithelioma the health condition is worsened (cf. Shafer L. A. et al., Ann. N.Y. Acad. Sci., V.277, pp.609–620, 1976). It should be noted that the preparation containing polypeptides (fraction V) has been administered in very high doses of about 400 mg/m$^2$ per day for the period of 21 days. In patients with severe combined immunodeficiency no positive dynamics in the immunological status was observed at all. (Cf. Astaldi A. et al., Treat. Rep. 62, p.1779, 1978).

Therefore, it is an urgent medical problem to provide a preparation containing polypeptides which would be more effective in respect of primary and secondary immunodeficiency.

OBJECT OF THE INVENTION

It is an object of the present invention to provide a preparation controlling the T-system of immunity which possesses a higher therapeutic activity and has no immunogeneity and pyrogeneity.

SUMMARY OF THE INVENTION

This object is accomplished by a preparation controlling the T-system of immunity which, in accordance with the present invention contains, as the active principle, peptides with a molecular mass ranging from 1,500 to 6,000 Dalton which have their absorption maximum in UV-light at 208 and 275 nm and electrophoretic mobility in a gel relative to bromophenol blue of: 0.062–0.102; 0.156–0.236; 0.354–0.374; 0.382–0.422; 0.432–0.472; 0.485–0.545; 0.850–0.930, and a pharmaceutical vehicle therefor.

The preparation controlling the T-system of immunity according to the present invention will be referred to hereinafter as T-activine.

In this preparation a physiological solution is used as a vehicle. The physiological solution comprises a 0.14 M solution of NaCl. In the preparation according to the present invention a content of the active principle is 100 to 200 μg/ml for injections.

The preparation possesses a specific immunostimulant activity relative to T-lymphocytes in vitro. In the test for restoration of sensitivity of T-rossette-forming cells (T-RFC) to azatioprin it shows activity in a dose of 1 μg per $3 \times 10^6$ lymphocytes. The preparation possesses a regulating effect on the T-system of immunity in the cases of its disturbances in patients suffering from malignant neoplasms, psoriasis and some other diseases. The regulating effect of T-activine is revealed in normalization of the quantity and balance of populations of T-lymphocytes at a lowered or increased activity thereof in patients. The preparation exerts a lytic effect on the primary tumor tissue and metastases, potentiates specific polychemotherapy and provides opportunities for a local radiotherapy of tumors. T-activine causes a stable and lasting restoration of T-immunity in patients with disturbances of the immune system due to the primary or secondary immunodeficient state and provides a pronounced therapeutic effect in the case of Louis-Bar syndrome and psoriasis. Furthermore, the preparation according to the present invention reduces intoxication symptoms, normalizes the body temperature and neurological status in all the above-mentioned diseases. The preparation results in no complications, pyrogenic effect or appearance of antibodies specific therefor, or cases of idiosincrasy.

The object of the present invention is accomplished by a method for producing a preparation controlling the T-system of immunity which involves:

(1) homogenization of a tissue of thymus gland in a solution of sodium chloride;
(2) keeping the homogenizate for a period of from 12 to 16 hours at a temperature of from 2° to 6° C.;
(3) removing the residue from the homogenizate;
(4) heating the solution to a temperature within the range of from 70° to 90° C. until a precipitate of thermolabile protein components is formed;
(5) removing thermolabile proteins;
(6) precipitation of proteins and peptides from the solution;
(7) dissolution of the resulting proteins and peptides;
(8) salting-out peptides from the solution in three stages: the first one—in a 20-30%, of saturation, solution of ammonium sulphate at a pH of from 6.9 to 7.1; the second—in a 45-55%, of saturation, solution of ammonium sulphate at pH of 3.9-4.1 and the third—in a 45-55%, of saturation, solution of ammonium sulphate at pH of 4.5-6.0;
(9) dissolution of the resulting precipitate of peptides;
(10) ultrafiltration of the solution of peptides through a membrane with a rated limit of retention relative to globular proteins of from 12,000 to 30,000 Dalton;
(11) gel-chromatography of the ultrafiltrate with separation of peptides with a molecular mass of from 1,500 to 6,000 Dalton in a buffer with pH of from 6.8 to 8.2 and an ionic strength of from 0.1 to 0.4 M;
(12) desalting of the separated peptides and lyophilization thereof;
(13) mixing the peptides with a pharmaceutical vehicle.

It is advisable that the salting-out in stage (8) be conducted at a concentration of proteins and peptides in the solution of from 15 to 25 mg/ml. This ensures a fuller yield of biologically active peptides.

It is advisable to maintain homogenizate in the stage (2) at a ratio of the solid and liquid portions of 1:3; the gel-chromatography of peptides in the stage (11) is preferably conducted in a buffer solution containing KCl or NaCl.

DETAILED DESCRIPTION OF THE INVENTION

Figure 3A:
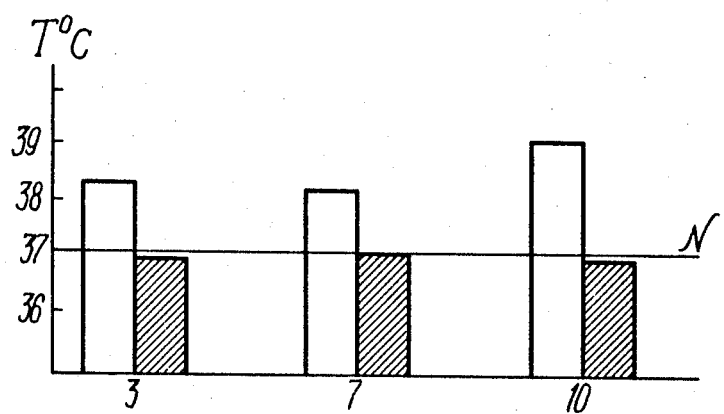

The preparation T-activine according to the present invention possesses a high-immunostimulant activity relative to T-lymphocytes in vitro. In the test of suppression of a spontaneous rosette-formation by azatioprin, its effect is revealed in a dose of 1 μg per $3 \times 10^6$ lymphocytes. The preparation is capable of restoring T-rosette-formation in the cases of disturbances of the immune system including those accompanying oncologic and other diseases. After the treatment with the preparation according to the present invention of lymphocytes of oncologic and other patients in vitro normalization of percentage of T-rosette-forming cells (T-RFC) is observed. (See Table 1 hereinbelow).

TABLE 1

Restoration of T-RFC in vitro by T-activine

| Patient No. | Diagnosis | T-RFC content in peripheral blood, % prior to the treatment | after treatment with T-activine (1 µg/2 × $10^5$ lymphocytes) |
|---|---|---|---|
| 1 | lymphosarcoma | 22 | 46 |
| 2 | lymphosarcoma | 34 | 55 |
| 3 | lymphosarcoma | 30 | 56 |
| 4 | lymphosarcoma | 16 | 37 |
| 5 | lymphogranulomatosis | 34 | 67 |
| 6 | lymphogranulomatosis | 54 | 83 |
| 7 | lymphogranulomatosis | 41 | 80 |
| 8 | lymphogranulomatosis | 42 | 73 |
| 9 | chronic lymphoid/leukosis | 44 | 70 |
| 10 | psoriasis | 42 | 51 |
| 11 | psoriasis | 42 | 59 |
| 12 | psoriasis | 12 | 60 |
| 13 | psoriasis | 23 | 59 |

The ability of restoring immunological response in animals under the effect of T-activine is observed in experimental data obtained on thymectomized mice and mice with congenital thymus aplosia. The thymectomized mice treated with the preparation become capable of forming T-rosette-forming cells within different periods after thymectomy. The data on the effect of T-activine in a dose of 40 µg/m² 5, 35 and 245 days after thymectomy on the immune response of thymectomized mice to sheep erythrocytes (T-RFC) are shown in FIG. 1, wherein along the axis of abscissae there is shown the number of rosette-forming cells per $10^3$ nucleated spleen cells, along the axis of ordinates there are shown the periods (days) after thymectomy; ☐ denotes administration of erythrocytes to normal animals; ▨ -denotes administration of erythrocytes to thymectomized animals; ▤ denotes administration of erythrocytes to thymectomized animals along with administration of T-activine.

From Graph 1 it is seen that the restoration of T-rosette-formation to normal values is observed in the animals 245 days after the thymectomy, i.e. even within the period of physiological ageing of the organism.

The effect of T-activine, manifested through the T-immune system, on the B-immune system upon immunization of "Nude" mice with sheep erythrocytes as determined by the test of antibody-forming cells (AFC) is shown in Graph 2, wherein the number of AFC is shown along the axis of abscissae; ☐ -immunization with sheep erythrocytes, ▨ -immunization with sheep erythrocytes with administration of T-activine.

Under the effect of T-activine the "nude"-line mice obtain ability of a normal immune response towards T-depending antigen-sheep erythrocytes and form specific antibody-forming cells. The data obtained point to the regulating effect of T-activine on the immune system of the organism.

The preparation according to the present invention reveals a specific action only on the organs of the immune system: thymus, lymphatic nodes and spleen. Upon the administration of T-activine in these organs there is noted stimulation of proliferation of lymphoid cells and DNA synthesis. In the remaining organs: liver, kidneys, heart, intestinal wall, lungs, spinal marrow and brain no morphological changes are observed by the light-microscopy data. The preparation is non-toxic and does not changes physiological functions of the nervous system, breathing, blood circulation in doses exceeding the therapeutic dose by 100 times. T-activine causes no disturbances in hemogenesis and composition of cells of peripheral blood in healthy animals which is illustrated by the data shown in Tables 2 (a, b and c) and 3 (a and b).

TABLE 2a

Erythrocytic composition of peripheral blood of experimental animals one week after the administration of T-activine

| Characteristics | Control M ± m | Therapeutical dose M ± m | p | 20-time dose M ± m | p |
|---|---|---|---|---|---|
| Hemoglobin, g % | 12.0 ± 0.57 | 11.7 ± 0.15 | >0.2 | 11.1 ± 0.5 | >0.1 |
| Erythrocytes, mln/µl | 4.2 ± 0.21 | 5.9 ± 0.16 | <0.001 | 6.0 ± 0.38 | <0.001 |
| Colour index | 0.86 ± 0.02 | 0.54 ± 0.01 | <0.001 | 0.54 ± 0.01 | <0.001 |

TABLE 2b

Erythrocytic composition of peripheral blood of experimental animals 2 weeks after the administration of T-activine

| Characteristics | Control M ± m | Therapeutical dose M ± m | p | 20-time dose M ± m | p |
|---|---|---|---|---|---|
| Hemoglobin, g % | 12.0 ± 0.57 | 13.9 ± 1.10 | 0.01 | 14.1 ± 0.40 | 0.001 |
| Erythrocytes, mln/µl | 4.2 ± 0.21 | 6.2 ± 0.16 | 0.001 | 6.3 ± 0.38 | 0.001 |
| Colour index | 0.86 ± 0.02 | 0.7 ± 0.02 | 0.001 | 0.75 ± 0.03 | 0.001 |

TABLE 2c

Erythrocytic composition of peripheral blood of experimental animals one year after the administration of T-activine

| Characteristics | Control M ± m | Therapeutic dose M ± m | p | 20-time dose M ± m | p |
|---|---|---|---|---|---|
| Hemoglobin, g % | 15.2 ± 0.66 | 15.5 ± 0.75 | 0.2 | 14.5 ± 0.75 | 0.2 |
| Erythrocytes, mln/µl | 6.2 ± 0.28 | 6.7 ± 0.2 | 0.1 | 5.6 ± 0.3 | 0.1 |
| Colour index | 0.84 ± 0.04 | 0.78 ± 0.02 | 0.1 | 0.76 ± 0.04 | 0.1 |

TABLE 3a

Leukocytic composition of peripheral blood of experimental animals after the administration of the therapeutic and 20-fold doses of T-activine 14 days after the injection

| Characteristics | Control M ± m | Therapeutic dose M ± m | p | 20-time dose M ± m | p |
|---|---|---|---|---|---|
| Leukocytes, $10^3$/µl | 4.7 ± 0.3 | 4.95 ± 0.27 | 0.2 | 4.64 ± 0.12 | 0.2 |
| Eosinophils, % | 3.0 ± 0.8 | 0.5 ± 0.2 | 0.01 | 0.5 ± 0.2 | 0.01 |
| Stab neutrophils, % | 1.5 ± 0.3 | 3.5 ± 1.3 | 0.1 | 3.5 ± 0.4 | 0.01 |
| Segmented neutrophils, % | 14.0 ± 2.6 | 18.5 ± 2.7 | 0.1 | 13.25 ± 3.6 | 0.05 |
| Lymphocytes, % | 76.5 ± 3.2 | 74.0 ± 2.5 | 0.05 | 81.0 ± 4.2 | 0.05 |
| Monocytes, % | 5.0 ± 1.1 | 3.5 ± 1.1 | 0.05 | 1.75 ± 0.2 | 0.05 |
| Index of nucleous shift | 0.1 ± 0.01 | 0.19 ± 0.13 | 0.05 | 0.26 ± 0.08 | 0.05 |

TABLE 3a-continued

Leukocytic composition of peripheral blood of experimental animals after the administration of the therapeutic and 20-fold doses of T-activine 14 days after the injection

| Characteristics | Control M ± m | Therapeutic dose M ± m | p | 20-time dose M ± m | p |
|---|---|---|---|---|---|
| of neutrophils | | | | | |

TABLE 3b

Leukocytic composition of peripheral blood of experimental animals after the administration of the therapeutic and 20-fold doses of T-activin one year after the injection of the preparation

| Characteristics 1 | Control M ± m 2 | Therapeutical dose M ± m 3 | p 4 | 20-time dose M ± m 5 | p 6 |
|---|---|---|---|---|---|
| Leukocytes, $10^3/\mu l$ | 4.7 ± 0.3 | 4.10 ± 0.25 | 0.1 | 3.9 ± 0.3 | 0.1 |
| Eosinophils, % | 3.0 ± 0.8 | 1.5 ± 0.2 | 0.02 | 1.8 ± 0.2 | 0.02 |
| Stab neutrophils, % | 1.5 ± 0.3 | 2.9 ± 0.5 | 0.02 | 3.1 ± 0.5 | 0.02 |
| Segmented neutrophils, % | 14.0 ± 2.6 | 17.1 ± 1.1 | 0.02 | 18.3 ± 2.1 | 0.03 |
| Lymphocytes, % | 76.5 ± 3.2 | 79.1 ± 2.3 | 0.1 | 69.1 ± 3.4 | 0.1 |
| Monocytes, % | 5.0 ± 1.1 | 3.4 ± 0.6 | 0.1 | 4.5 ± 0.5 | 0.1 |
| Index of nucleous shift of neutrophils | 0.1 ± 0.01 | 0.15 ± 0.05 | 0.2 | 0.13 ± 0.03 | 0.2 |

A more important property of the preparation according to the present invention, T-activine, is its positive effect in vivo as regards normalization of the characteristics of the T-immune system and implicit effect on the B-system of immunity of the body in various pathological states and its direct therapeutic effect in primary immunodeficient states: ataxia-telangiectasis (Louis-Bar syndrome) and secondary immunodeficient states including those in the case of malignant tumors such as lymphogranulomatosis, lymphosarcoma, retinoblastoma and many others.

In the evaluation of the immunological status of patients with a primary immunodeficient state there is observed a functional disorder of the T- and B-immune systems which is manifested in a reduced ability of T-lymphocytes to blast-transformation and a reduced amount of serum immunoglobulin (IgA). The data obtained in this evaluation are shown in Table 4 hereinbelow.

TABLE 4

Dynamics of variation of concentration of serum immunoglobulins in children with Louis-Bar syndrome, mg %

| Patient | Prior to immunotherapy | | | After immunotherapy (7 days) | | | After immunotherapy (14 days) | | |
|---|---|---|---|---|---|---|---|---|---|
| | IgA | IgG | IgM | IgA | IgG | IgM | IgA | IgG | IgM |
| | Norm | | | 50–200 | 950–1,980 | 70–200 | | | |
| 1 | 45 | 350 | 49 | 74 | 330 | 505 | 82 | 560 | 103 |
| 2 | 110 | 1,680 | 280 | 190 | 2460 | 500 | 48 | 2,250 | 360 |
| 3 | 56 | 960 | 70 | | | | 38 | 1,030 | 140 |
| 4 | 74 | 1,140 | 90 | 8 | 1,500 | 250 | 16 | 1,350 | 350 |
| 5 | 58 | 690 | 250 | | | | | | |
| average | 69 ± 444 | 964 ± 93 | 146 ± 27 | | | | 46 ± 198 | 1,297 ± 133 | 238 ± |

As follows from the above Table 4, after the administration of the preparation, within the first 7 days there is noted the tendency towards restoration of the functional activity of T-lymphocytes in the test of the reaction of blast-transformation. The amount of serum immunoglobulins IgA, G, M is also increased thus pointing to the stumulation of the B-immunity system.

The clinical effect after administration of the preparation is revealed by the 3-d day after the injection of the preparation and is manifested in positive dynamics of the akinetic-rigid syndrome and hyperkinetic syndrome, restoration of the speed of propagation of an impulse along the nervous fibres and an increased force of muscle contractions by 1.5–2 times.

In the evaluation of the immunological status of patients with a secondary immunodeficient state in the case of lymphogranulomatosis there are observed quantitative and functional disturbances of the T-system of immunity. Table 5 shows the data pointing to the decreased absolute content of T-lymphocytes and their functional activity in the test of blast-transformation with phytohemagglutinin (PHA). As follows from the quantitative content of immunoglobulins IgA, IgG, IgM no functional disturbance of the B-system is observed. (See Table 5).

After the introduction of T-activine there is observed restoration of the absolute content of T-lymphocytes. In the group of patients with a reduced percentage of T-rosette-forming cells (T-RFC) there is observed restoration of the parameter to the normal value. The functional activity is also restored to the norm. The data obtained demonstrate the regulating effect of T-activine relative to the cellular immunity. These data are shown in Table 6 hereinbelow.

TABLE 5

Clinical and immunological characteristics of children suffering from lymphogranulomatosis (LGM) prior to immunotherapy

| Patient's No. 1 | age, years 2 | LGM stage 3 | Hystological type 4 | Absolute number of lymphocytes 5 | % of E-RFC 6 | Absolute number of T-lymph 7 |
|---|---|---|---|---|---|---|
| | | | NORM | above 1500 | 65 | above 1000 |
| 1 | 7 | IIAa | mx.cl. | 726 | 29 | 211 |
| 2 | 6 | IIIAb | mx.cl. | 1300 | 30 | 390 |
| 3 | 3 | IIBb | mx.cl. | 1080 | 36 | 388 |

TABLE 5-continued

Clinical and immunological characteristics of
children suffering from lymphogranulomatosis
(LGM) prior to immunotherapy

| No. | Patient's age, years | LGM stage | Histological type | Absolute number of lymphocytes | % of E-RFC | Absolute number of T-lymph. |
|---|---|---|---|---|---|---|
| 4  | 3.5 | IIIAb | mx.cl.           | 2940 | 32 | 940  |
| 5  | 7   | IIIAb | mix.cl.          | 1480 | 25 | 370  |
| 6  | 3.5 | IIAa  | mx.cl.           | 875  | 46 | 402  |
| 7  | 13  | IIIBb | mx.cl.           | 1533 | 46 | 720  |
| 8  | 7   | IIIAb | —                | 2394 | 46 | 1110 |
| 9  | 8   | IIBb  | —                | 1495 | 52 | 748  |
| 10 | 7   | IIIBb | lymph. pred.     | 2490 | 60 | 1494 |
| 11 | 7   | IIAb  | mx.cl.           | 2223 | 40 | 889  |
| 12 | 9   | IVBb  | mx.cl.           | 2071 | 41 | 848  |
| 13 | 4   | IIIAb | mx.cl.           | 1330 | 68 | 904  |

| | Blast/transformation reaction with PHA | | | | Concentration of serum immunoglobulins, mg % | | |
|---|---|---|---|---|---|---|---|
| No. 1 | back-ground 8 | PHA 9 | Index 10 | % of B-RFC 11 | IgA 12 | IgM 13 | IgG 14 |
|    |     |       | above 40 | 10–30 | 50–200 | 70–200 | 950–1980 |
| 1  | 424 | 18869 | 30.3 | 40 | 195 | 40  | 950  |
| 2  | 346 | 14355 | 41.4 | 20 | 320 | 160 | 2100 |
| 3  | 115 | 3350  | 29.1 | 24 |     |     |      |
| 4  |     |       |      | 28 | 208 | 220 | 1400 |
| 5  | 152 | 1357  | 9    | 20 | 150 | 90  | 1520 |
| 6  | 130 | 2352  | 18.0 | 30 | 116 | 60  | 1320 |
| 7  |     |       |      | 22 | 376 | 160 | 2000 |
| 8  | 80  | 2527  | 31.3 | 23 | 125 | 135 | 1050 |
| 9  | 439 | 9810  | 22.3 | 25 |     |     |      |
| 10 |     |       | 5.7  | 30 | 210 | 120 | 1680 |
| 11 | 286 | 6830  | 23   | 25 | 62  | 70  | 1500 |
| 12 |     |       |      | 14 |     |     |      |
| 13 | 585 | 16773 | 28.6 | 37 | 72  | 130 | 1380 |

B-RFC - B-rosette-forming cells;
mx.cl. - mixed cellular type;
lymph.pred. - lymphoid predomination;
PHA - phytohemagglutinin.

TABLE 6

Clinical and immunological characteristics of
children suffering from lymphogranulomatosis
(LGM) after immunotherapy

| No. 1 | Patient's age, years 2 | LGM stage 3 | Histological type 4 | Absolute number of lymphocytes 5 | % of E-RFC 6 | Absolute number of T-lymph. 7 |
|---|---|---|---|---|---|---|
|    |     | NORM  |         | above 1500 | 65 | above 1000 |
| 1  | 7   | IIAa  | mx.cl.  | 1178 | 66 | 777  |
| 2  | 6   | IIIAb | mx.cl.  | 1316 | 65 | 855  |
| 3  | 3   | IIBb  | mx.cl.  | 1566 | 67 | 1049 |
| 4  | 3.5 | IIIAb | mx.cl.  | 2288 | 68 | 1556 |
| 5  | 7   | IIIAb | mx.cl.  | 1184 | 68 | 805  |
| 6  | 3.5 | IIAa  | mx.cl.  | 2544 | 68 | 1248 |
| 7  | 13  | IIIBb | mx.cl.  | 1540 | 72 | 1108 |
| 8  | 7   | IIIAb | —       | 1591 | 68 | 1081 |
| 9  | 8   | IIBb  | —       | 1664 | 64 | 1064 |
| 10 | 7   | IIIBb | lymph. pred. | 3180 | 55 | 1749 |
| 11 | 7   | IIAb  | mx.cl.  | 1071 | 67 | 717  |
| 12 | 9   | IVBb  | mx.cl.  | 1040 |    |      |
| 13 | 4   | IIIAb | mx.cl.  | 1308 | 54 | 707  |

| | Blasttransformation reaction with PHA | | | | Concentration of serum immunoglobuline, mg % | | |
|---|---|---|---|---|---|---|---|
| No. 1 | back-ground 8 | PHA 9 | Index 10 | % of B-RFC 11 | IgA 12 | IgM 13 | IgG 14 |
|    |     |       | above 40 | 10–30 | 50–200 | 70–200 | 950–1980 |
| 1  | 149 | 23965 | 160 | 26 | 200 | 60  | 860  |
| 2  | 375 | 19962 | 55  | 22 | 400 | 270 | 2500 |
| 3  | 184 | 8720  | 29  | 19 |     |     |      |
| 4  |     |       | 107 | 28 | 210 | 144 | 1680 |
| 5  | 714 | 66282 | 92  | 23 | 135 | 90  | 1120 |
| 6  | 248 | 8437  | 34  | 35 | 120 | 120 | 1740 |
| 7  | 330 | 4900  | 14  | 25 | 210 | 310 | 1440 |
| 8  | 308 | 9512  | 30  | 48 | 90  | 85  | 1200 |
| 9  | 200 | 7545  | 38  | 19 | 50  | 30  | 480  |
| 10 | 420 | 17902 | 47  | 20 | 320 | 80  | 1440 |
| 11 | 273 | 17046 | 62  | 20 | 280 | 500 | 200  |
| 12 |     |       |     |    |     |     |      |
| 13 | 1513| 34433 | 22  | 40 | 45  | 70  | 1050 |

Abbreviations are the same as in Table 5.

Figure 3B:
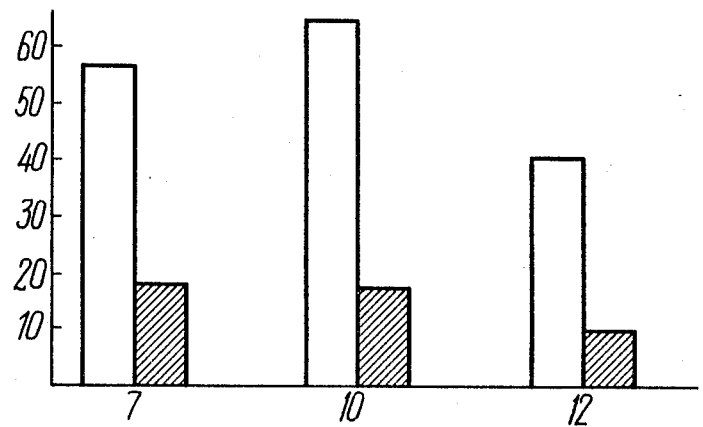
Figure 4:
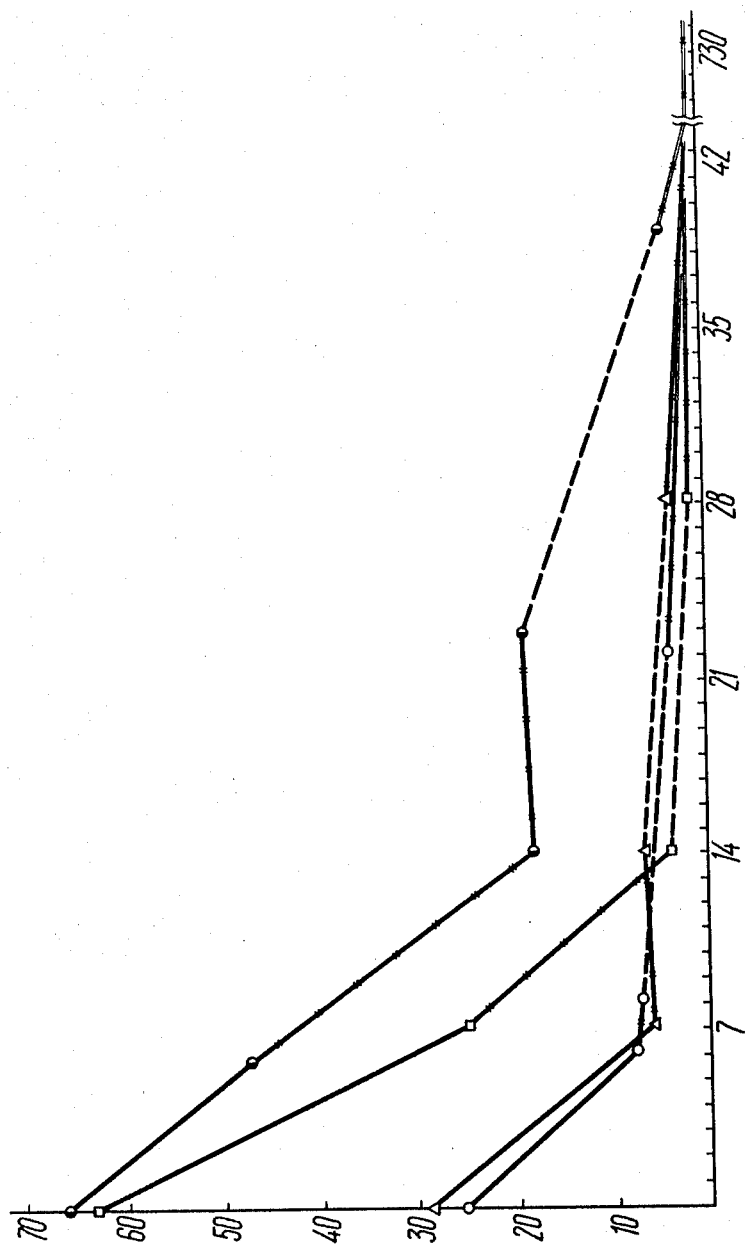

An especially important property of the preparation according to the present invention is its therapeutic effect in respect of oncological diseases in patients with immunodeficient states. The optimal therapeutic effect is revealed upon administration of the preparation as injections in courses with a daily dose of 20–40 μg per 1 $m^2$ of the body surface area. In patients suffering from malignant neoplasms with specific intoxication, body temperature is normalized even during the first day, health condition is improved along with appetite. Together with immunotherapy of children suffering from lymphogranulomatosis in the stage of the process generalization (stages II–IV) with T-activine, even within the first day after the administration of the preparation there is observed division, softening and separation of individual lymphatic nodes out of the conglomerate of injured lymphatic nodes and, further decrease of the area of the injured nodes by 60–70% of the initial value by the 7–14-th day. Upon analysis of cytograms of the injured lymphatic nodes in the course of therapy with T-activine there is observed an increased percentage of lymphocytes in lymphatic nodes from 70–80% to 95–98% along with lymphonodulous effect, specific Berezovsky-Schternberg cells are destroyed too. In children with a pronounced biological activity of the process there is observed normalization of the erythrocyte sedimentation rate (ESR) and discontinuation of intoxication. The data are shown in FIGS. 3a and 3b, wherein: a—effect on symptoms of specific intoxication, b—effect on the biological activity of the process (ESR),▭- prior to the introduction of T-activine, ▨- after the administration of T-activine. In parallel to the effect of T-activine in the patients, the absolute content of peripheral T-lymphocytes is normalized along with normalization of the percentage of E-rosette-forming cells and index of stimulation of lymphocytes. On completion of the immunotherapy of the patients suffering from malignant neoplasms with T-activine, an opportunity is provided for continuation of a more efficient polychemotherapy or local radiotherapy. There is observed a rapid occurrence of remission of the progress of the malignant disease. The corresponding data are shown in Tables 7 and 8 hereinbelow. The positive dynamics of the lymphonodulous effect is shown in FIG. 4, wherein along the axis of abscissae the area of lymphatic nodes in $cm^2$ is shown, along the axis of ordinates 2 days after the beginning of the treatment; the line ——————— means periods of administration of T-activine; the line —#——#— denotes the period of absence of the pharmaceutical therapy; the line -------- denotes the period of chemotherapy.

The preparation of T-activine according to the present invention causes a stable and lasting restoration of the immunity. In the treatment of malignant tumors it possesses a clearly pronounced direct antitumor effect, reduces time of remission occurrence, potentiates a specific polychemotherapy and provides an opportunity for a local radiotherapy.

TABLE 7

Effect of T-activine on time limits of occurrence of lymphogranulomatosis remission in children

| Group of patients | Time limits of remission occurrence (months) | | | | |
|---|---|---|---|---|---|
| | 1.5–2.0 | 6.0 | 12 | No remission | Death |
| | number of children | | | | |
| 1. After immunotherapy with T-activine 13 children | 12 | 1 | — | — | — |
| 2. Non-treated with T-activine 22 children | 2 | 17 | 1 | 1 | 1 |

TABLE 8

Effect of T-activine on frequency of complications in children suffering from lymphogranulomatosis

| Groups of patients | Kinds of complications | |
|---|---|---|
| | Cytotaxic disease (number of children) | Induced immunodeficiency (number of children) |
| 13 children subjected to immunotherapy | 1 | — |
| 22 children subjected to no immunotherapy | 11 | 14 |

Taking into account the regulating effect of the preparation, it is now possible to use T-activine for the treatment of secondary hypoplastic states of hemogenesis. Along with immunotherapy of an acute hypoplastic state by the preparation in combination with an immunodeficient state there is observed restoration of immunity and characteristics of the peripheral blood and the bone-marrow hemogenesis.

The application of the preparation in the treatment of other diseases associated with disorders of the immunity system such as psoriasis, systemic lupus erythematosis and the like provides a good clinical effect even after the first course of immunotherapy. The clinical effect of T-activine in this case is revealed in reduced time of occurrence of remission which is of a great importance for the patients manifesting resistance against a specific chemotherapy. Upon administration of the preparation to patients there are never observed any complications, pyrogenic effect or appearance of antibodies specific relative to T-activine. No cases of idiosincrasy are noted.

The method for producing the preparation according to the present invention is effected in the following manner. As the source of raw materials use is made of a calf thymus gland. Prior to the use, the gland tissue can be stored at a temperature of −20° C. up to 3 months. Thymus is cleared-off the capsule and cut to pieces of 0.5–1 g on the cold. To the disintegrated raw material any physiological salt solution is added, usually a 0.14 M NaCl, in the ratio of 1:3. Then the material is homogenized in a homogenizer of a vortex type for 3 minutes at the speed of 8,000 r.p.m. In this stage the material is disintegrated into a uniform mass. The stage of homogenization is conducted at a temperature within the range of from 2° to 4° C.

The above-specified ratio of the raw material and the physiological solution ensured the production of a uniform homogenizate and a most full yield of biologically active substances from the raw material at the stage of residence. The residence of the homogenizate is effected at a temperature of from 2° to 6° C. for a period of from 12 to 16 hours. The residence (autolysis) conditions are found experimentally and variations of the time or temperature parameters result in a lowered yield and biological activity of the desired product. During autolysis there occurs an additional destruction of cells, cytoplasmatic and nucleous membranes, as well as modification under the effect of enzymes, proteins and peptides. This provides for a higher yield of biologically active substances and transformation thereof to products with an increased specific biological activity. Then the insoluble coarse-size fragments are removed by centrifugation at 14,000 to 20,000 g for one hour at the temperature of 4° C. The supernatant is drained through a gauze or kapron filter to retain large-size fatty fragments.

Then the supernatant is heated in a water bath under vigorous stirring to a temperature of from 70° to 90° C., usually to 80° C. and maintained at this temperature for 15 minutes. In this stage there occurs denaturation of thermolabile ballast protein components. After cooling to a temperature of 4° C. the thermolabile components are removed by centrifugation at 14,000 to 20,000 g for one hour. The centrifugation can be substituted by any other known method ensuring elimination of denaturated proteins, for example by filtration on filters with a sufficient pore size. The supernatant containing biologically active thermostable proteins and peptides is subjected to precipitation with acetone. It is also possible to use another organic solvent such as ethanol. The procedure is carried out at a temperature within the range of from −20° to −25° C. One volume of the supernatant is drop-wise added to 5 volumes of acetone simultaneously with stirring of a mixture. The mixture is maintained for 2 days at the temperature of −20° C. At this stage there occurs dissolution of fats and other ballast substances in the organic solvent. The precipitate contains biologically active proteins and peptides. The liquid portion is removed, a residue is dried under vacuum at the temperature of 4° C. It is very important, during the precipitation of biologically active peptides with acetone, to strictly observe the temperature conditions and the ratio between the volume of the supernatant and acetone (of from 1:5 to 1:7). Change of these parameters causes a reduced biological activity of the material and contamination thereof with ballast substances. The dried residue is dissolved in a 0.01 M sodium-phosphate buffer, pH=7.0 at a temperature of from 18° to 22° C. and stirred for one hour. The insoluble products are removed by centrifugation at 10,000 to 16,000 g for 40 minutes. The supernatant is collected and diluted with the buffer solution to a concentration of from 15 to 25 mg/ml.

It is advisable to use the above-specified concentration of proteins and peptides in solution, since it ensures minimal losses of biologically active peptides in a further salting-out. The resulting solution is added with a saturated solution of ammonium sulphate to the final concentration thereof of 20–30% at a pH of from 6.9 to 7.1. The mixture is stirred for one hour at a temperature of from 2° to 4° C. The insoluble portion is removed by centrifugation at 16,000 g for 30-40 minutes. Then the supernatant is added with a 10% acetic acid to a pH of from 3.9 to 4.1. In doing so there is observed a partial precipitation of a biologically active material. A complete precipitation is ensured by introduction, into the supernatant, of a dry powder of ammonium sulphate so as to obtain 45-55% of saturation with the account of the final volume of the mixture. The mixture is stirred for one hour at a temperature of from 2° to 4° C. The supernatant is removed and the residue is dissolved in a 0.01 M tris-HCl buffer solution at pH of 8.0. The third stage of salting-out is effected in a 45-55% solution, of saturation, of ammonium sulphate at pH of from 4.5 to 6.0. The solution is thoroughly stirred at a temperature of from 2° to 4° C. for one hour and the residue is collected by centrifugation at 16,000 g for 30 to 40 minutes. The carrying-out of the salting-out in three stages makes it possible to ensure an additional purification from ballast substances and is necessary to obtain the desired product with predetermined properties. Then the residue is dissolved in a 10 $\mu$M tris-HCl buffer solution at pH of 8.0 and the concentration of the protein is brought to 8-12 mg/ml using the same buffer.

The resulting solution is subjected to ultrafiltration through membrane filters with a nominal retention limit relative to globular proteins within the range of from 12,000 to 30,000 Dalton in the atmosphere of nitrogen under a pressure of from 3.0 to 3.5 atmospheres at a temperature of 2° to 4° C. It is preferable to use membranes Pellicon PSED (Millipore), though it is possible to use any other filter possessing the same characteristics (VM-30, PM-30). Then the membrane is washed with a triple volume of a 0.01 M tris-HCl buffer solution at pH of 8.0. This ensures a complete passing of the biologically active components into the filtrate. 80-85% of ballast substances are retained on the filter. The filtrate is collected and lyophilized. The resulting material is dissolved in a minimal volume of distilled water and then subjected to desalting by way of exclusion chromatography in columns with sephadex G-15 (medium) of 2.5×30 cm. It is also possible to use other molecular sieves having similar characteristics. Elution is conducted in distilled water. The material containing protein components is collected and again lyophilically dried. The dry powder is dissolved in a buffer solution at a pH of from 6.8 to 8.2 with an ionic strength of 0.1 to 0.4 M containing NaCl or KCl. The solution is subjected to gel-chromatography in a 2.5×100 cm column with Sephadex G-50 (medium) preliminarily equallized with the same buffer solution. As the carrier for gel-chromatography in this stage it is possible to use other molecular sieves with the same characteristics.

Optimal separation of biologically active peptides is ensured in a buffer solution with the above-specified characteristics. After gel-chromatography the desired product with a molecular mass of from 1,500 to 6,000 Dalton is collected. The product with a molecular mass in this particular range contains peptides possessing a regulating effect on the T-immune system of the organism. The solution of peptides is again desalted by gel-chromatography in columns with Sephadex G-15, lyophilized, dissolved in a salt physiological solution and sealed in ampules in a dose of from 100 to 200 $\mu$g/ml.

For a better understanding of the present invention, some specific examples illustrating the method for producing the preparation controlling the T-immune system are given hereinbelow.

EXAMPLE 1

500 g of freshly freezed calf thymus ($-20°$ C.) are purified from capsule and homogenized in a 0.14 M NaCl solution (volume of 1.5 l) at a temperature of 4° C. Thereafter the homogenizate is centrifuged at 20,000 g for two hours. The residue is removed. The supernatant in the volume of about 1.5 l is heated at a temperature of 80° C. for 15 minutes in a water bath. Then the solvent is cooled and denaturated thermolabile components are removed by centrifugation at 20,000 g for 1 hour. The supernatant (volume of about 1.35 l) is treated with a 5-time volume of acetone cooled to $-20°$ C. for two days. The resulting precipitate is separated from the liquid portion by decantation and dried in vacuum. The residue is dissolved in 100 ml of a 10 $\mu$M sodium-phosphate buffer of pH=7.0 under continuous stirring for one hour at room temperature. The insoluble portion is removed by centrifugation at 16,000 g for 40 minutes and the supernatant is diluted with distilled water to a protein concentration of 25 mg/ml by the biuret method. The resulting solution is added with 39.6 ml of a solution of ammonium sulphate saturated at a temperature of 4° C., pH=7.0. The mixture is stirred for one hour at 4° C. The insoluble portion is removed by centrifugation at 16,000 g. The supernatant is acidified with acetic acid to pH of 4.0, added with 24.82 g of ammonium sulphate and stirred for 1 hour at 4° C. The resulting residue is collected by centrifugation, dissolved in 80 ml of a 10 $\mu$M tris-HCl buffer with pH of 8.0 and again precipitated by adding 80 ml of a solution of ammonium sulphate saturated at 4° C., pH=5.0. The residue is again collected by centrifugation, dissolved in a 10 $\mu$M of tris-HCl buffer with pH of 8.0 and the protein concentration, as determined by the biuret method, is brought to 10 mg/ml with the same buffer solution. The resulting solution is subjected to ultrafiltration through a membrane Pellicon PSED (Millipore) at a temperature of 4° C. under nitrogen pressure of from 3.5 to 4 atm. The membrane is washed by three portions by 150 ml of a 10 $\mu$M of tris-HCl buffer with pH of 8.0.

The volume and concentration of protein in the fraction under and above the filter are respectively equal to 510 ml, 0.7 mg/ml and 0.6 ml, 12 mg/ml. Both fractions after desalting and lyophilization are tested for biological activity in the system of T-rosette-formation. Only the fraction under the filter possesses biological activity, while the fraction retained by the filter is inactive. A portion of the biologically active fraction in the amount of 30 mg is dissolved in a 0.2 M KCl solution prepared on tris-HCl buffer, pH=8.0, and gel-chromatography is carried out in a 1×100 cm column with Sephadex G-50 balanced with the same buffer. Peptides with a molecular mass of from 1,500 to 6,000 Dalton are collected, desalted on a column with Sephadex G-15 and lyophilized. The minimal active dose is 1-2 $\mu$g per $3 \times 10^6$ lymphocytes in vitro. The total yield of the desired product is 110 mg/kg of thymus. The activity as defined by the test of inhibition of a spontaneous rosette-formation by azotioprin is not more than 1 $\mu$g per $3 \times 10^6$ lymphocytes. The resulting peptides are dissolved in a 0.14 M NaCl.

To determine heterogeneity of the thymus preparation by its molecular mass, 10 mg of the preparation in 1 ml of a buffer solution (0.14 M NaCl 0.01 M tris-HCl), pH=8.0, are applied onto a 1×100 cm column with Sephadex G-50 (fine) balanced with the same buffer solution. The rate of elution was made equal to 6.0 ml/hr, the time of collection of the fraction was 15 minutes. The active components of the preparation were distributed in test-tubes with serial numbers of from 32 to 50. The column was preliminarily graduated with a mixture of standard substances with a known molecular mass. This enabled determination the presence, in said test tubes, of the components with a mass of from 1,500 to 6,000 Dalton.

To determine heterogeneity of the preparation there was also carried out an analytical disk-electrophoresis in a 15% polyacrylamide gel at pH of 8.9 on an instrument available from the company "Reanal" (Hungary). Onto every tube of the gel there are applied 400–600 μg of the preparation in 0.02–0.03 ml of the electrode buffer. Electrophoresis is conducted at a temperature of 5°–7° C. and current of 2 mA per tube within the following 1–1.5 hours. The front of ion movement was marked by bromophenol blue. On completion of electrophoresis the gel is extracted from the tubes, fixed and dyed with a 0.1% solution of amido-black 10B in a 7% acetic acid for 40 minutes, whereafter the dyestuff is washed with a 7% acetic acid. There are found 7 bands corresponding to 7 components of the preparation; their electrophoretic mobility is evaluated from the formula:

$$K_{e/ph} = \frac{l_p/l^\bullet}{l_{bphb}/l}$$

wherein
 l is gel length before dyeing
 l* is gel length after dyeing
 $l_p$ is the distance passed by the protein band
 $l_{bphb}$ is the distance passed by bromophenol blue.
The test results are shown in Table 9.

TABLE 9

| Band No. from cathode | 1 | 2 | 3 | 4 | 5 | 6 | 7 |
|---|---|---|---|---|---|---|---|
| $K_{e/ph}$ | 0.082 | 0.169 | 0.364 | 0.402 | 0.452 | 0.515 | 0.89 |

For the determination of isoelectric points of the components of the thymus preparation, isoelectric focusing in a thin layer of polyacrylamide gel in a pH range of from 3.5 to 10 on an instrument "Multiphor". On completion of focusing the gel is fixed in trichloroacetic acid, 25% isopropanol for 16 hours, dyed with 0.05% Coumassi blue R-250 in 10% acetic acid, 25% isopropanol overnight and then treated with a 10% acetic acid. The pH gradient is defined by the position of protein-tracers with a known isoelectric point. The thymus preparation is focused in 13 bands with the following values of isoelectric points: 4.0; 4.3; 4.6; 4.7; 4.8; 5.0; 5.2; 5.5; 6.1; 6.3; 6.7; 7.4; 9.0.

The thymus preparation containing polypeptides proved to have two absorption maximums when analyzed in UV-light at 203 and 275 nm.

EXAMPLE 2

The procedure of Example 1 is repeated, except that the homogenizate is maintained for 12 hours at a temperature of 2° C.; the column with Sephadex G-50 is balanced with 0.14 M NaCl in a 0.05 M tris-HCl buffer solution, pH 7.2.

The yield of the desired product is 118 μg/kg of thymus. The activity by the test of inhibition of spontaneous rosette formation with azatioprin is not more than 1 μg per 3×10⁶ lymphocytes.

EXAMPLE 3

The procedure described in the foregoing Example 1 is repeated, except that the first salting-out is conducted in a 20%, of saturation, solution of ammonium sulphate at a pH 6.9; the second—in a 40%, of saturation, solution of ammonium sulphate at a pH of 3.9; the third—in a 45%, of saturation, solution of ammonium sulphate at a pH=4.5; the column with Sephadex G-50 is balanced with a 0.14 M NaCl in a 0.01 M tris-HCl, pH 7.2.

The yield of the desired product is 115.5 mg/kg of thymus.

The activity, as determined by the test of inhibition of a spontaneous rosette-formation with azatioprin, is not more than 1 μg per 3×10⁶ lymphocytes.

What is claimed is:
1. An active principle effective for control of the T-system of immunity, said active principle being obtained by removing thermolabile proteins from a solution of homogenized thymus gland tissue in a sodium chloride solution, precipitating proteins and peptides from the solution, dissolving the same in a solvent therefor, salting out the peptides from the solution, dissolving the peptides, subjecting the resulting solution to ultrafiltration, and subjecting the resulting ultrafiltrate to gel chromatography, and said active principle consisting of polypeptides with a molecular mass of from 1,500 to 6,000 Dalton, having the maximum of absorption in UV-light as 208 and 275 nm and the electrophoretic mobility in a polyacrylamide gel relative to bromophenol blue of: 0.062–0.102; 0.156–0.236; 0.354–0.374; 0.382–0.422; 0.432–0.472; 0.485–0.545; 0.850–0.930.

2. A preparation according to claim 1, wherein as the pharmaceutical vehicle a physiological solution is used.

3. A preparation according to claim 2, wherein the physiological solution is a 0.14 M NaCl solution.

4. A preparation according to claim 1, wherein the content of the active principle is about 100 to 200 μg/ml for injections.

5. A method for producing the active principle of claim 1 for control of the T-system of immunity, which comprises:
 (1) homogenizing a thymus gland tissue in a sodium chloride solution;
 (2) keeping the homogenizate for 12 to 16 hours at a temperature of from 2° to 6° C.;
 (3) removing the residue from the homogenizate;
 (4) heating the remaining solution to a temperature within the range of from 70° to 90° C. to from a residue of thermolabile protein components;
 (5) removing the thermolabile proteins from the solution;
 (6) precipitating proteins and peptides from the solution;
 (7) dissolving the thus precipitated proteins and peptides in a solvent therefor;
 (8) salting-out the peptides from the solution in three stages, the first being conducted in a 20–30%, by saturation, solution of ammonium sulphate at a pH of from 6.9 to 7.1, the second in a 45–55%, by saturation, solution of ammonium sulphate at a pH of from 3.9 to 4.1, and the third in a 45–55%, by saturation, solution of ammonium sulphate at a pH of from 4.5 to 6.0;
 (9) dissolving the resulting residue of peptides;

(10) subjecting the formed solution to ultrafiltration through a membrane with a rated retention limit relative to globular proteins of from 12,000 to 30,000 Dalton;

(11) subjecting the obtained ultrafiltrate to gel-chromatography to separate the peptides with a molecular mass of from 1,500 to 6,000 Dalton in a buffer solution at a pH of from 6.8 to 8.2 and an ionic strength of from 0.1 to 0.4 M;

(12) desalting the separated peptides and subjecting the same to lyophilization.

6. The method for producing the active principle according to claim 5, wherein salting-out at the stage (8) is effected at a concentration of proteins and peptides in the solution of from 15 to 25 mg/ml.

7. The method for producing the active principle according to claim 5, wherein the homogenate in stage (2) is kept at the ratio between the solid and liquid portions of 1:3.

8. The method for producing the active principle according to claim 5, wherein gel-chromatography of peptides in stage (11) is effected in a buffer solution containing KCl or NaCl.

9. A preparation comprising an effective amount of the T-system immunity active principle of claim 1 and a pharmaceutical vehicle therefor.

* * * * *